US00PP26794P3

(12) United States Plant Patent
Olesen

(10) Patent No.: US PP26,794 P3
(45) Date of Patent: Jun. 7, 2016

(54) FLORIBUNDA ROSE PLANT NAMED 'POULCAS044'

(50) Latin Name: ***Rosa* hybrid**
Varietal Denomination: Poulcas044

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 82 days.

(21) Appl. No.: 14/121,282

(22) Filed: Aug. 15, 2014

(65) Prior Publication Data

US 2016/0050813 P1 Feb. 18, 2016

(51) Int. Cl.
*A01H 5/00* (2006.01)

(52) U.S. Cl.
USPC ..... Plt./148

(58) Field of Classification Search
USPC ..... Plt./148
See application file for complete search history.

(56) References Cited

PUBLICATIONS

PLUTO Plant Variety Database Dec. 24, 2015. p. 1.*

* cited by examiner

*Primary Examiner* — Annette Para

(57) ABSTRACT

A new garden rose plant of the floribunda class which has abundant, mauve flowers and attractive foliage. This new and distinct variety has shown to be uniform and stable in the resulting generations from asexual propagation.

1 Drawing Sheet

Botanical designation: *Rosa* hybrid.
Variety denomination: 'Poulcas044'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulcas044', originated as a single seedling from the stated cross.

The new variety may be distinguished from its female seed parent by flower colour. The female seed parent has pink flowers, while the new variety has mauve flowers.

The new variety may be distinguished from the male pollen parent by flower colour. The pollen parent has medium red flowers.

The objective of the hybridization of this rose variety was to create a new and distinct variety for garden use with unique qualities, such as:

1. Uniform and abundant mauve flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulcas044' from all other varieties of which we are aware.

As part of the rose development program, Mogens N. Olesen germinated the seeds from the aforementioned hybridization during winter of 2006 and conducted evaluations on the resulting seedlings in a controlled environment in Fredensborg, Denmark. 'Poulcas044' was selected in the spring of 2007 by the inventor as a single plant from the progeny of the aforementioned hybridization.

Asexual reproduction of 'Poulcas044' by traditional budding and rooted cuttings was first done by Mogens N. Olesen in the nursery in Fredensborg, Denmark in July, 2007. This initial and other subsequent asexual propagations conducted in controlled environments have demonstrated that the characteristics of 'Poulcas044' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulcas044'.

Specifically illustrated in the drawing are flowers at various stages of development, flower in parts, leaves, and stems. Plants shown are 2 years of age.

DETAILED DESCRIPTION OF THE VARIETY

The following is a description of 'Poulcas044', as observed in its growth in in a field nursery in Marion County, Oreg. Observed plants are 2 years of age, and were grown on their own roots. Observed plants are 3 years of age, and were grown on *Rosa multiflora* understock. Color references are made using The Royal Horticultural Society (London, England) Colour Chart, 2001, except where common terms of color are used.

For a comparison, several physical characteristics of the rose variety 'Poulbella', U.S. Plant Pat. No. 12,904 dated Sep. 3, 2002, are compared to 'Poulcas044' in Chart 1.

CHART 1

| | 'Poulcas044' | 'Poulbella' |
|---|---|---|
| Petal Count | 40 petals | 35 to 40 petals |
| Flower Diameter | 85 mm | 50 to 80 mm |
| General Tonality of Flower Color | Red-Purple Group 63B | Red-Purple Group 57C |

Flower and Flower Bud

Blooming habit: Continuous.

Flower bud:

*Size*.—Upon opening, 35 mm in length from base of receptacle to end of bud. Bud diameter is 15 mm.

*Bud form*.—Globose.

*Bud color*.—As sepals divide petals are Red-Purple Group 67A.

*Sepal inner surface*.—Color: Yellow-Green Group 144C with intonations of Greyed-Red Group 181B. Surface: Lightly pubescent.

*Sepal outer surface*.—Color: Yellow-Green Group 144A with intonations of Red Group 180A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—30 mm long by 10 mm wide.

*Receptacle*.—Texture: Smooth. Size: 6 mm in height by 6 mm wide. Color: Yellow-Green Group 144A. Shape: Urn shaped.

*Pedicel*.—Surface: Small prickles. Length: 30 to 35 mm. Diameter: 3 mm on average. Color: Yellow-Green Group N144A. Strength: Strong.

Flower bud development: Flower buds are borne in clusters of 1 to 5 flower buds per stem.

Flower bloom:

*Fragrance*.—Moderate rose perfume.

*Duration*.—The blooms have a duration on the plant of approximately 7 to 10 days. Petals fall cleanly away from plant after flowers have fully matured.

*Size*.—Flower diameter is 85 mm when open. Flower depth is 35 mm.

Petalage: Under normal conditions, flowers have 40 petals total, 5 of which are petaloids.

General tonality of flower: Open flowers are Red-Purple Group 63B.

Petal color:

*Upon opening, outer & inner petals*.—Upper surface: Red-Purple Group N66C. Lower surface: Red-Purple Group 68B.

*Basal petal spots, upon opening*.—Upper surface: Yellow Group 1C. Lower surface: Yellow Group 1C.

*After opening, outer petals*.—Upper surface: Red-Purple Group N66C. Lower surface: Red-Purple Group 68B.

*After opening, inner petals*.—Upper surface: Red-Purple Group N66C. Lower surface: Red-Purple Group 68B.

*Basal petal spots, after opening*.—Upper surface: Yellow Group 1C. Lower surface: Yellow Group 1C.

Petals:

*Petal reflex*.—Slightly reflexed.

*Margin*.—Entire and uniform.

*Shape*.—Generally rounded. Apex shape: Rounded. Base shape: Broadly acute.

*Size*.—40 mm (l)×40 mm (w).

*Texture*.—Smooth.

*Thickness*.—Average.

Petaloids:

*Size*.—20 mm (l) by 15 mm (w).

*Quantity*.—About 5.

*Shape*.—Apex is rounded, base is acute.

*Color*.—Upper surface, Red-Purple Group N66C. Lower surface, Red-Purple Group 68B. Basal petaloid spots are Yellow Group 1C upper and lower surface.

Reproductive organs:

*Pollen*.—None observed.

*Anthers*.—Size: 2 mm in length. Color: Greyed-Yellow Group 162A. Quantity: 60 on average.

*Filaments*.—Color: White Group 155A. Length: 5 mm.

*Pistils*.—Length: 4 mm. Quantity: 25 on average.

*Stigmas*.—Color: Greyed-Yellow Group 162D.

*Styles*.—Color: Green-White Group 157A.

Plant

Plant growth: Upright, bushy. Plants are about 45 cm in height, and 40 cm wide.

Stems:

*Color*.—Juvenile growth: Yellow-Green Group N144A. Mature growth: Yellow-Green Group N144A.

*Length*.—On average, canes are 30 cm from the base of the plant to the flowering portion.

*Diameter*.—6 to 7 mm.

*Internodes*.—On mature canes, there is an average distance of 40 mm between nodes.

*Surface texture*.—Young wood: Smooth. Older wood: Smooth.

Long prickles:

*Incidence*.—9 prickles per 10 cm of stem.

*Size*.—Average length of prickles on mature stems is 10 mm.

*Shape*.—Upper portion is linear. Lower portion is concave.

*Color*.—Juvenile prickles: Greyed-Purple Group 184B. Mature prickles: Greyed-Red Group 182C.

Plant foliage:

*Compound leaf*.—125 mm (l)×85 (w).

*Quantity*.—2 leaves per 10 cm of stem on average.

*Leaf bearing angle to the stem*.—60 degrees.

*Color of juvenile foliage*.—Upper side: Yellow-Green Group 144B. Lower side: Yellow-Green Group 145B.

*Color of mature foliage*.—Upper side: Yellow-Green Group 146A. Lower side: Yellow-Green Group 146B.

Plant leaves and leaflets:

*Stipules*.—Size: 17 mm in length. 3 mm width. Quantity: 2 per compound leaf. Shape: Linear, slightly broad based with outward extending apices. Margins: Finely serrated with many stipitate glands. Color: Yellow-Green Group 146A.

*Petiole*.—Length: 15 mm. Diameter: 2 mm.

*Upper surface*.—Color: Red-Purple Group 59C.

*Lower surface*.—Color: Red-Purple Group 59C and Yellow-Green Group 145C.

*Rachis*.—Length: 60 mm. Upper surface: Color: Yellow-Green Group 145C with intonations of Red Group 182A.

*Lower surface*.—Color: Yellow-Green Group 145C. Observations: Small prickles.

*Leaflet*.—Quantity: Normal number of leaflets per leaf in middle of the stem is 7 leaflets. Margins: Serrated. Size: Average size of the terminal leaflet on normal leaves is 50 mm in length by 48 mm wide. Shape: Generally elliptical. Base: Rounded. Apex: Mucronate. Texture: Smooth. Thickness: Average. Arrangement: Odd pinnate. Venation: Reticulate. Glossiness: Glossy.

Disease resistance: Above average resistance to powdery mildew *Sphaerotheca pannosa,* downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the floribunda rose class named 'Poulcas044', substantially as illustrated and described herein, due to its abundant mauve flowers, disease resistance, and extended period of bloom.

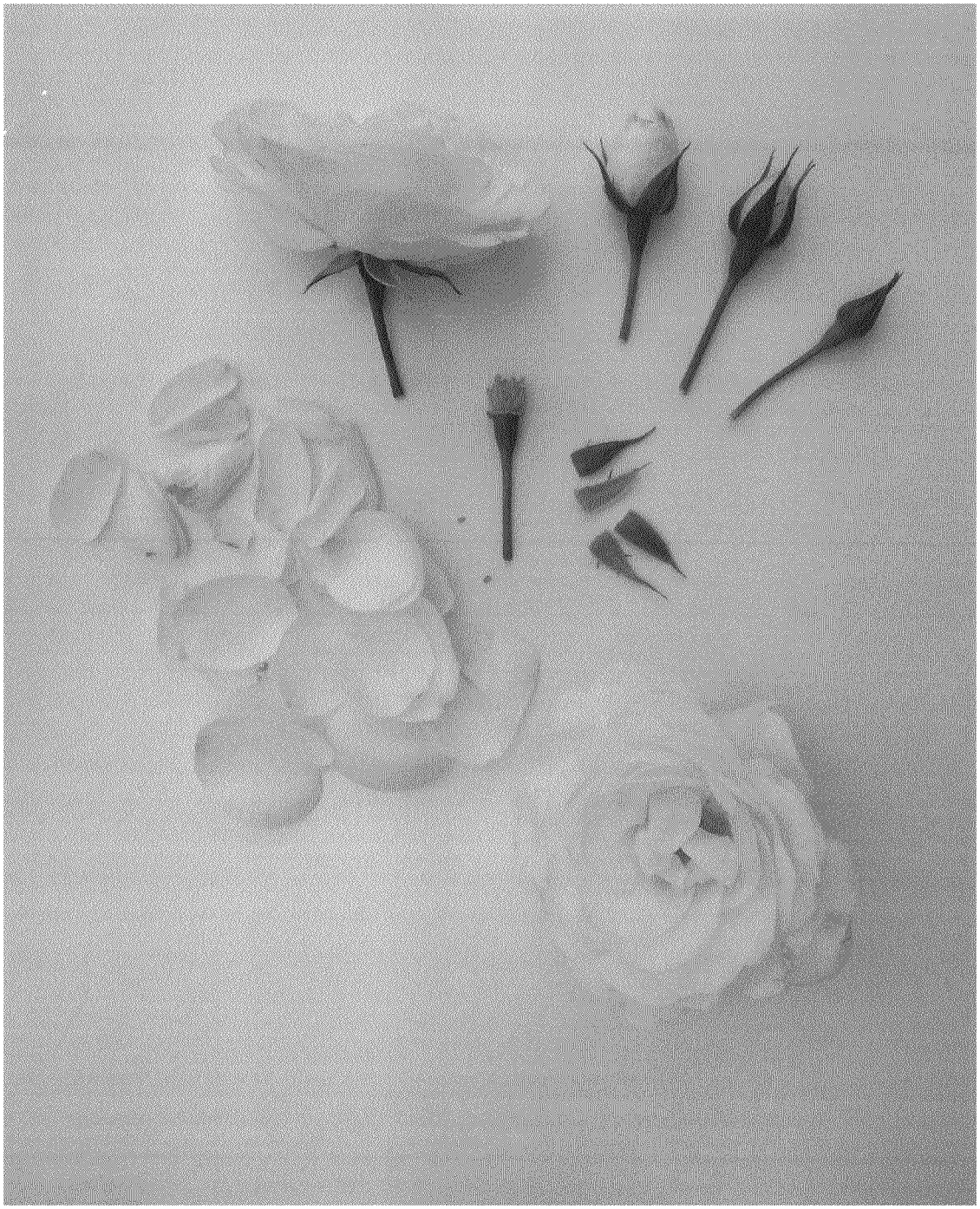

* * * * *